(12) United States Patent
Glover et al.

(10) Patent No.: US 10,987,350 B2
(45) Date of Patent: Apr. 27, 2021

(54) METHOD FOR TREATING POST-TRAUMATIC STRESS DISORDER

(71) Applicants: Hillel Glover, Saratoga Springs, NY (US); Lillian Hahn, North Miami Beach, FL (US)

(72) Inventors: Hillel Glover, Saratoga Springs, NY (US); Elliot Hahn, Miami, FL (US)

(*) Notice: Subject to any disclaimer, the term of this patent is extended or adjusted under 35 U.S.C. 154(b) by 0 days.

(21) Appl. No.: 16/608,162

(22) PCT Filed: Apr. 25, 2018

(86) PCT No.: PCT/US2018/029257
§ 371 (c)(1),
(2) Date: Oct. 24, 2019

(87) PCT Pub. No.: WO2018/200607
PCT Pub. Date: Nov. 1, 2018

(65) Prior Publication Data
US 2020/0197387 A1    Jun. 25, 2020

Related U.S. Application Data

(60) Provisional application No. 62/489,501, filed on Apr. 25, 2017.

(51) Int. Cl.
*A61K 31/485* (2006.01)

(52) U.S. Cl.
CPC .................... *A61K 31/485* (2013.01)

(58) Field of Classification Search
CPC ......... A61K 31/485; A61P 25/00; A61P 43/00
USPC .......................................................... 514/282
See application file for complete search history.

(56) References Cited

U.S. PATENT DOCUMENTS 5,028,612 A * 7/1991 Glover ................. A61K 31/485
514/282

\* cited by examiner

*Primary Examiner* — Charanjit Aulakh
(74) *Attorney, Agent, or Firm* — Ted Whitlock Registered Patent Attorney, PA

(57) ABSTRACT

Disclosed and described is a novel dose titration procedure for administering the opioid antagonist, nalmefene, to a patient diagnosed with post-traumatic stress disorder (PTSD).

10 Claims, No Drawings

METHOD FOR TREATING POST-TRAUMATIC STRESS DISORDER

FIELD OF THE INVENTION

The subject invention concerns a novel dose titration procedure for administering the opioid antagonist, nalmefene, to a patient diagnosed with post-traumatic stress disorder (PTSD).

BACKGROUND OF THE INVENTION

Nalmefene is used primarily in the management of alcohol dependence. It has also been investigated for the treatment of other addictions such as pathological gambling.

Nalmefene is an opiate derivative similar in both structure and activity to the opioid antagonist naltrexone. Advantages of nalmefene relative to naltrexone include longer half-life, greater oral bioavailability and no observed dose-dependent liver toxicity. As with other drugs of this type, nalmefene can precipitate acute withdrawal symptoms in patients who are dependent on opioid drugs, or more rarely when used post-operatively to counteract the effects of strong opioids used in surgery.

Intravenous doses of nalmefene have been shown effective at counteracting the respiratory depression produced by opiate overdose. Doses greater than 1.5 mg do not appear to give any greater benefit in this application.

Between the years 1988-1990, in an open-label pilot study, nalmefene was administered to 18 combat veterans diagnosed with post-traumatic stress disorder (PTSD.) The published pilot study reported the administration of low doses of the drug starting with the lowest dose of one milligram twice a day with gradual increments of the dose up to a maximum of 200 milligrams twice a day.

The hypothesis of the study was that nalmefene (an opiate antagonist with activity at the kappa opiate receptor) would reverse the subjective experience of emotional numbness observed in patients diagnosed with PTSD. Patients suffering with emotional numbness may also demonstrate a persistent inability to experience positive emotions (e.g. inability to experience happiness, satisfaction, or loving feelings), a markedly diminished interest or participation in significant activities, and possibly also with feelings of detachment or estrangement from others Other related subjective experiences that may be reported by patients who feel emotionally numb can include feeling emotionally dead, shutdown, hollow and/or empty no feelings. These subjective experiences are associated with degrees of lack of care and concern for the welfare of self and others.

Based on the study results, nalmefene was observed to significantly reduce, and in some cases remit, the symptom of emotional numbness, and to facilitate the veterans' abilities to experience a range of normal human responses including feelings of empathy, love, care and concern for others. Unexpectedly, the drug was also found to significantly improve all core symptoms of PTSD including nightmares, intrusive thoughts, flashbacks; the inability to engage in topics dealing with combat experiences without the onset of symptoms of emotional distress or behavioral avoidance; dissociative amnesia; mistrust of others; and states of hyper arousal and reactivity associated with the traumatic events (*Diagnostic Statistical Manual*-5, American Psychiatric Association, pub, 2013). The results of the pilot study were published in the *Israel Journal of Psychiatry*, volume 30, issue 4, Nov. 1993.

An improved, higher dosing titration schedule can unexpectedly provide a greater benefit to patients suffering from PTSD

SUMMARY OF THE INVENTION

One object of the subject invention is to provide improved benefit to patients diagnosed with PTSD, by employing a higher dose titration schedule for the administration of nalmefene. In accordance with the nalmefene dosing titration schedule of the subject invention, nalmefene is administered at a higher initial dose than the dosing schedule published in the pilot study, and administering nalmefene at the same, higher dose increments at regular intervals described above. Specifically, the subject invention comprises administering nalmefene orally to a PTSD patient at an initial dose of 100 milligrams per day, preferably using 50 milligram doses, twice a day, with increases every 3-4 days of 100 mg per day (50 milligrams twice a day), not to exceed 1000 mg per day (500 mg twice a day).

DETAILED DESCRIPTION OF THE INVENTION

The subject invention comprises administering, on a dosing titration schedule, nalmefene, to a patient diagnosed with post-traumatic stress disorder (PTSD), using
  a starting dose of 100 mg per day, preferably in divided doses of 50 mg twice per day; and
  increasing the dose by 100-150 mg per day, every 2-5 days, up to a maximum daily dose of 1000 mg, per day.

The subject dosing titration schedule is preferably increased from the initial dose of 100 mg per day every 3-4 days. Each increase is preferably 100 mg per day, at a divided dose of 50 mg twice per day.

In a preferred embodiment, the nalmefene is administered as an oral liquid or solid (e.g., tablet or capsule) preparation. In another embodiment, the nalmefene is administered as an intravenous injection, a subcutaneous injection, or intramuscular injection preparation. In yet another embodiment, the nalmefene is administered topically as a topical preparation, e.g., a cream, gel, or ointment, or the like, or is administered transdermally using a transdermal patch preparation. In each of these preparations, the nalmefene can be formulated in an immediate release or controlled-release dosage form.

Additional work using the higher dose titration schedule of nalmefene revealed several unexpected clinical advantages resulting from this increased dose administration schedule, including but not limited to:

An optimum dose of nalmefene, wherein PTSD symptoms are reduced or reversed, can be achieved within 2-3 weeks for individuals diagnosed with PTSD. The reduced or reversed. PTSD symptoms are based on both clinical observation of the patient and on reporting of reduced or reversed symptoms by the patient.

It was discovered that administering the drug at the higher dose of at least 50 mgs twice a day unexpectedly bypassed the emergence of opiate withdrawal symptoms.

The hypothesis of this study was that emotional numbness is an endogenous opiate mediated phenomenon. It was fully expected that administering an opiate antagonist to a group of combat veterans diagnosed with PTSD who also reported frequent feelings of being emotionally numb would be associated with symptoms of opiate withdrawal, and such opiate withdrawal symptoms were expected by the patients, as self-reported.

The dosing administration schedule of the subject invention was successful in avoiding the occurrence of fluctuating mood states (e.g. anxiety, hostility and rage, depression, and paranoia) with dose increases.

The mental state of the PTSD patient was stabilized in a much briefer period of time using a dose administration schedule in accordance with the subject invention, which maximized the patient's cooperation and/or minimized the patient's possible drop out from the treatment.

In addition, it should be emphasized that dose increases of approximately 50 milligrams twice a day every 3-4 days should also avoid the possibility of an adverse reaction such as the onset of frequent and intense mood swings observed with dose increments significantly greater than 50 milligrams twice a day.

The invention claimed is:

1. A method for treating patient diagnosed with post-traumatic stress disorder (PTSD), said method comprising:
   a) administering nalmefene at a starting dose of 100 mg per day to a patient diagnosed with or having symptoms of PTSD; and
   b) increasing the dose by 100 mg per day, every 2-5 days, up to a maximum of 1000 mg, per day.

2. The method of claim 1, wherein the initial dose of step a) is administered in a divided dose comprising 50 mg twice per day.

3. The method of claim 1 wherein the increased dose of step be b) is administered in a divided dose schedule of 50 mg twice per day.

4. The method of claim 1 wherein the dose is increased every 3-4 days.

5. The method of claim 1 wherein treating the patient diagnosed with PTSD decreases or reverses the symptoms of PTSD experience by the patient.

6. The method of claim 5 wherein the decreased or reversed symptom is selected from the group consisting of emotional numbness, persistent inability to experience positive emotions (e.g. inability to experience happiness, satisfaction, or loving feelings), diminished interest or participation in significant activities, feelings of detachment, and estrangement from others.

7. The method of claim 1 wherein the patient does not experience opioid withdrawal symptoms following administration of nalmefene.

8. The method of claim 1 wherein the administration of nalmefene provides an avoidance of occurrence of fluctuating mood states.

9. The method of claim 8, wherein the mood states are selected from the group consisting of anxiety, hostility and rage, depression, and paranoia.

10. The method of claim 1 wherein the administered nalmefene is formulated in a dosage form selected from the group consisting of: an intravenous injection preparation, an intramuscular injection preparation, a subcutaneous injection preparation, a topical preparation, a transdermal preparation, and an oral dosage form preparation.

* * * * *